United States Patent
Lorenzo et al.

(10) Patent No.: US 11,207,494 B2
(45) Date of Patent: Dec. 28, 2021

(54) MEDICAL DEVICE DELIVERY MEMBER WITH FLEXIBLE STRETCH RESISTANT DISTAL PORTION

(71) Applicant: DePuy Synthes Products, Inc., Raynham, MA (US)

(72) Inventors: Juan Lorenzo, Raynham, MA (US); Tyson Montidoro, Raynham, MA (US); Daniel Solaun, Raynham, MA (US); David Blumenstyk, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 150 days.

(21) Appl. No.: 16/502,767

(22) Filed: Jul. 3, 2019

(65) Prior Publication Data
US 2021/0001082 A1 Jan. 7, 2021

(51) Int. Cl.
*A61M 25/00* (2006.01)
*A61B 17/12* (2006.01)
(Continued)

(52) U.S. Cl.
CPC ... *A61M 25/0052* (2013.01); *A61B 17/12181* (2013.01); *A61M 25/0012* (2013.01);
(Continued)

(58) Field of Classification Search
CPC .......... A61M 25/0052; A61M 25/0012; A61M 25/0108; A61M 25/0147; A61M 25/0662; A61B 17/12181; A61B 2017/00526; A61B 2017/00623; A61B 2017/00336; A61B 17/12031; A61B 2017/12054;
(Continued)

(56) References Cited

U.S. PATENT DOCUMENTS

| 3,429,408 A | 2/1969 | Maker et al. |
| 5,108,407 A | 4/1992 | Geremia et al. |
| (Continued) | | |

FOREIGN PATENT DOCUMENTS

| EP | 1985244 A2 | 10/2008 |
| EP | 2498691 | 9/2012 |
| (Continued) | | |

OTHER PUBLICATIONS

"Affixed, 2011, Houghton Mifflin Harcourt Publishing Company, American Heritage® Dictionary of the English Language, Fifth Edition" (Year: 2011).*

(Continued)

*Primary Examiner* — Tiffany Legette
(74) *Attorney, Agent, or Firm* — Troutman Pepper Hamilton Sanders LLP

(57) ABSTRACT

A delivery member is provided for delivering and deploying an intravascular medical device. The delivery member includes a flexible distal portion including a wound wire coil surrounded by a flexible sleeve and inhibited from extending lengthwise by a stretch resistant member positioned through the lumen of the coil. The delivery member can include hypotubes positioned on either side (distally and proximally) from the wound wire coil to which the stretch resistant member and the wound wire coil can be attached.

20 Claims, 4 Drawing Sheets

(51) Int. Cl.
*A61M 25/01* (2006.01)
*A61M 25/06* (2006.01)
*A61B 17/00* (2006.01)

(52) U.S. Cl.
CPC .... *A61M 25/0108* (2013.01); *A61M 25/0147* (2013.01); *A61M 25/0662* (2013.01); *A61B 2017/00526* (2013.01)

(58) Field of Classification Search
CPC ........ A61B 17/12109; A61B 17/12113; A61B 17/1214; A61B 2017/1205; A61B 17/12022
See application file for complete search history.

(56) References Cited

U.S. PATENT DOCUMENTS

| | | | |
|---|---|---|---|
| 5,122,136 A | 6/1992 | Guglielmi et al. |
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,718 B2 | 3/2018 | Lorenzo |
| 10,282,851 B2 | 5/2019 | Gorochow |
| 10,285,710 B2 | 5/2019 | Lorenzo et al. |
| 10,292,851 B2 | 5/2019 | Gorochow |
| 10,517,604 B2 | 12/2019 | Bowman et al. |
| 10,806,402 B2 | 10/2020 | Cadieu et al. |
| 10,806,461 B2 | 10/2020 | Lorenzo |
| 2001/0049519 A1* | 12/2001 | Holman ............ B29C 45/14598 604/534 |
| 2002/0072705 A1* | 6/2002 | Vrba ................ A61M 25/0108 604/96.01 |
| 2002/0165569 A1 | 11/2002 | Ramzipoor et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0116711 A1* | 6/2006 | Elliott ............... A61B 17/12145 606/200 |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0233168 A1* | 10/2007 | Davis, III ......... A61B 17/12154 606/191 |
| 2007/0270903 A1 | 11/2007 | Davis III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1* | 3/2009 | Ford ................ A61B 17/12113 604/57 |
| 2009/0312748 A1 | 12/2009 | Johnson et al. |
| 2010/0114017 A1 | 5/2010 | Lenker et al. |
| 2010/0324649 A1 | 12/2010 | Mattsson |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |

(56) References Cited

U.S. PATENT DOCUMENTS

| | | |
|---|---|---|
| 2012/0283768 A1 | 11/2012 | Cox et al. |
| 2013/0066413 A1 | 3/2013 | Jin et al. |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0277084 A1 | 9/2014 | Mirigian et al. |
| 2014/0277085 A1* | 9/2014 | Mirigian .......... A61B 17/12113 606/200 |
| 2014/0277092 A1 | 9/2014 | Teoh et al. |
| 2014/0277093 A1 | 9/2014 | Guo et al. |
| 2015/0005808 A1 | 1/2015 | Chouinard et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1* | 1/2016 | Garza ................ B23K 26/361 606/200 |
| 2016/0157869 A1 | 6/2016 | Elgård et al. |
| 2016/0228125 A1 | 8/2016 | Pederson, Jr. et al. |
| 2016/0310304 A1 | 10/2016 | Mialhe |
| 2016/0346508 A1* | 12/2016 | Williams ............... A61B 17/22 |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2017/0367712 A1* | 12/2017 | Johnson ............. A61B 17/1214 |
| 2018/0028779 A1* | 2/2018 | von Oepen ........... A61F 2/2427 |
| 2018/0036508 A1 | 2/2018 | Ozasa et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0325706 A1 | 11/2018 | Hebert et al. |
| 2019/0159784 A1 | 5/2019 | Sananes et al. |
| 2019/0192162 A1 | 6/2019 | Lorenzo et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0187951 A1 | 6/2020 | Blumenstyk |
| 2021/0001082 A1 | 1/2021 | Lorenzo et al. |

FOREIGN PATENT DOCUMENTS

| | | | |
|---|---|---|---|
| EP | 3092956 A1 | 11/2016 | |
| EP | 3501427 A1 | 6/2019 | |
| JP | 2006-334408 A | 12/2006 | |
| JP | 2012-523943 A | 10/2012 | |
| JP | 2013-78584 A | 5/2013 | |
| WO | WO 2009/132045 A2 | 10/2009 | |
| WO | WO-2012158152 A1 * | 11/2012 | ....... A61B 17/12172 |
| WO | WO 2017/066386 A1 | 4/2017 | |
| WO | WO 2018/022186 A1 | 2/2018 | |

OTHER PUBLICATIONS

"Sleeve, 2011, Houghton Mifflin Harcourt Publishing Company, American Heritage® Dictionary of the English Language, Fifth Edition" (Year: 2011).*

"Loop, 2011, Houghton Mifflin Harcourt Publishing Company, American Heritage® Dictionary of the English Language, Fifth Edition" (Year: 2011).*

"Approximate, 2014, HarperCollins Publishers, Collins English Dictionary—Complete and Unabridged, 12th Edition" (Year: 2014).*

Extended European Search Report dated Nov. 18, 2020 in European Patent Application No. 20178690.

Extended European Search Report dated Dec. 18, 2020 in European Patent Application No. 20181340.

Extended European Search Report issued in corresponding European Patent Application No. 20 21 2970 dated May 28, 2021.

Extended European Search Report issued in European Patent Application No. 21 15 6857 dated Jun. 22, 2021.

* cited by examiner

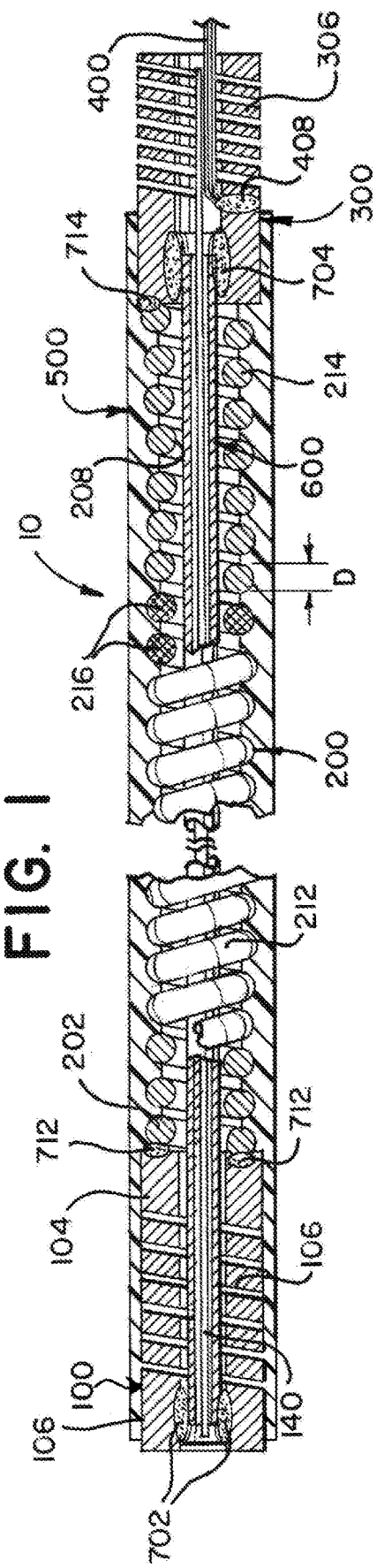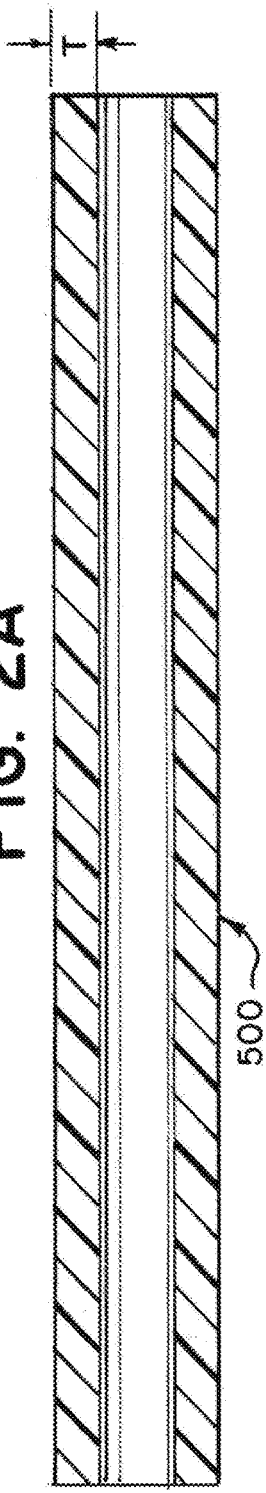

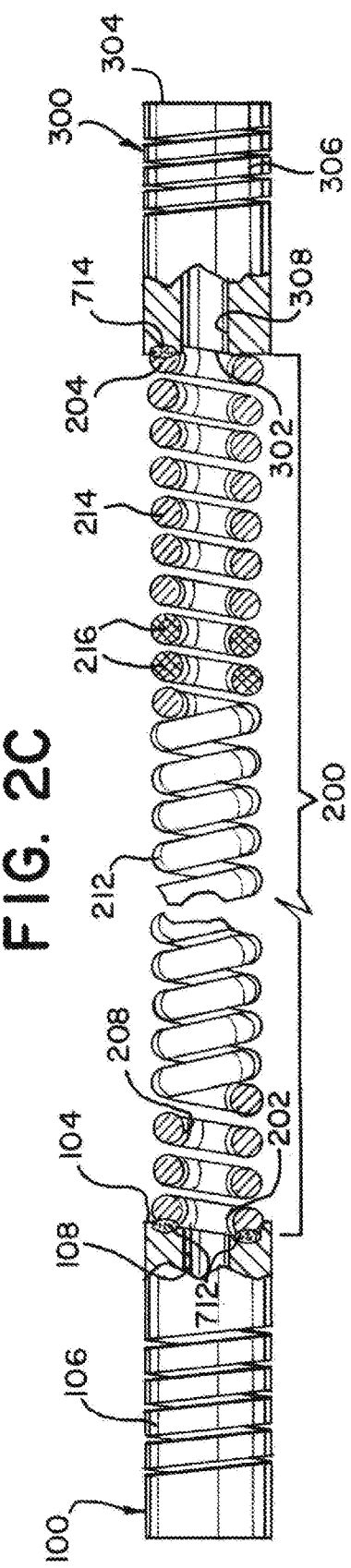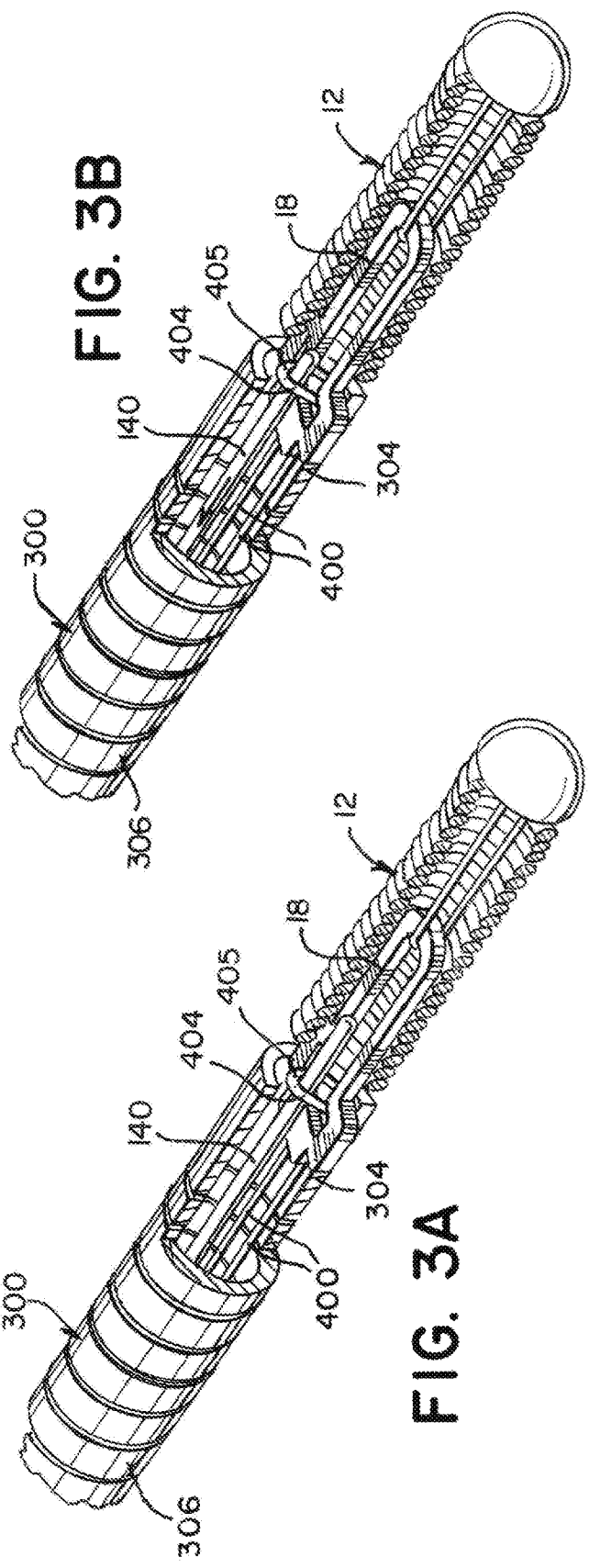

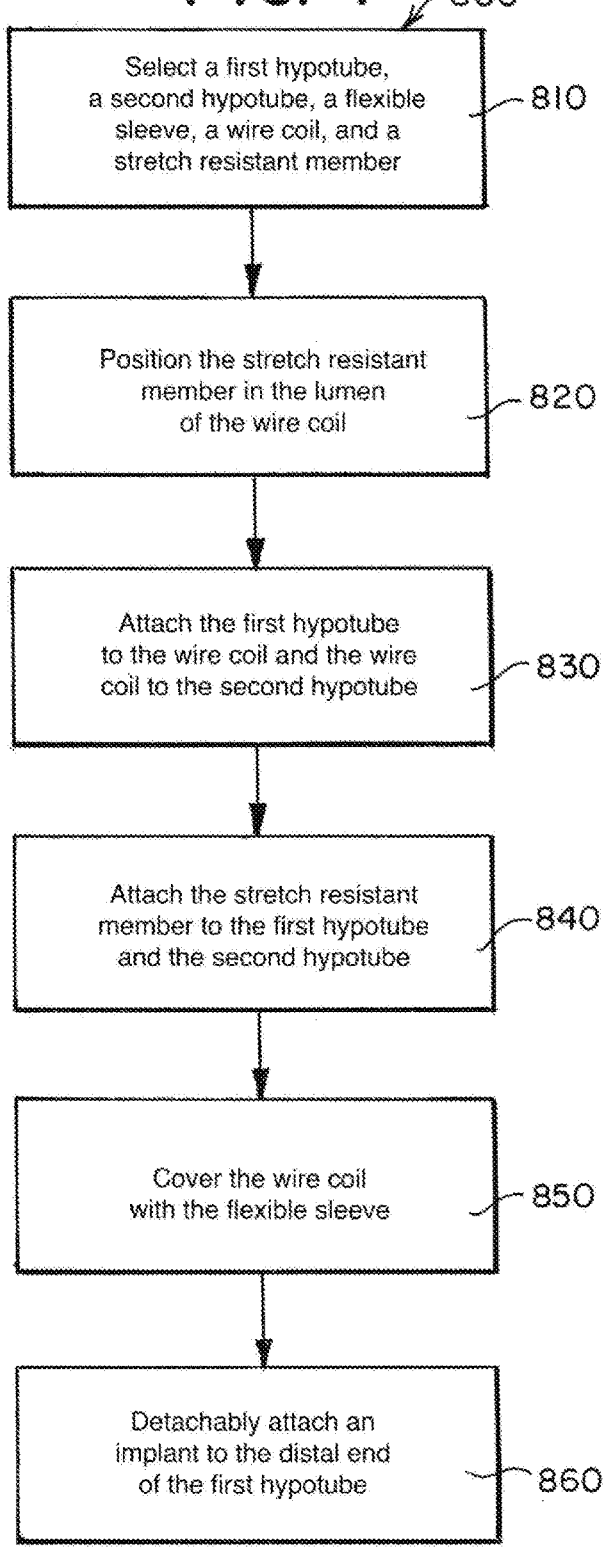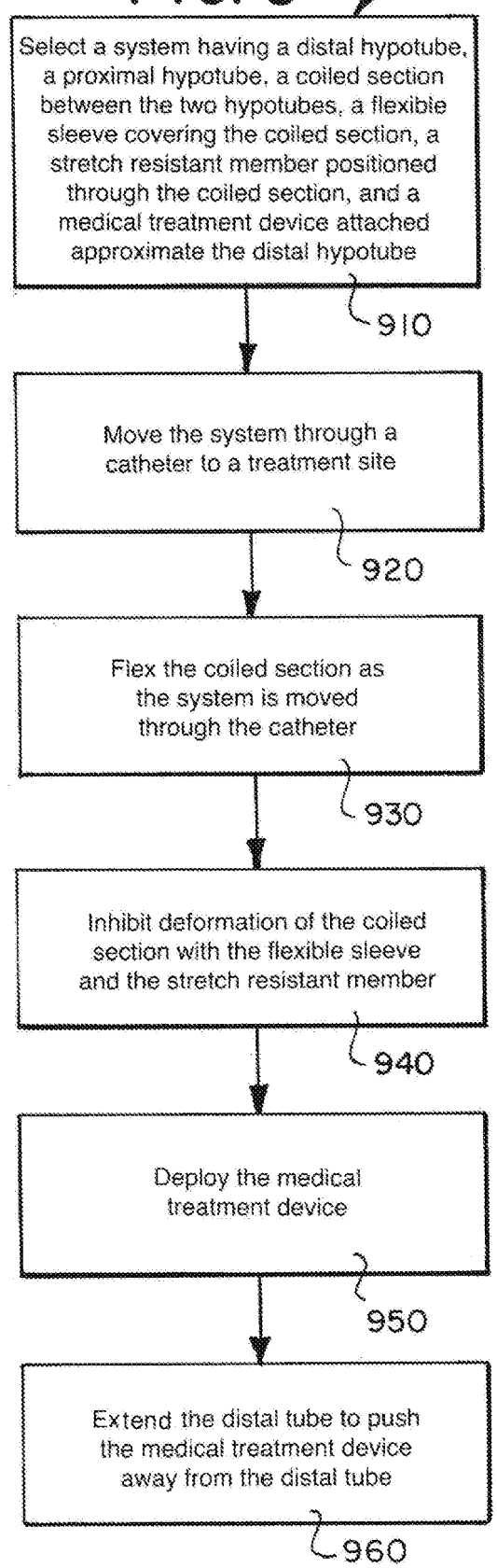

MEDICAL DEVICE DELIVERY MEMBER WITH FLEXIBLE STRETCH RESISTANT DISTAL PORTION

FIELD OF INVENTION

This invention generally relates to intravascular medical device systems navigable through body vessels of a human subject. More particularly, this invention relates to delivery systems and delivery members for delivering and deploying an implantable medical device to a target location of a body vessel and methods of using the same.

BACKGROUND

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, e.g. brain tissue, it can be difficult and often risky to perform surgical procedures to treat defects of the cranial blood vessels. Advancements in catheter-based implant delivery systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting a delivery catheter into the vasculature of a patient and guiding it through the vasculature to a predetermined delivery site. A vascular occlusion device, such as an embolic coil, can be attached to an implant engagement/deployment system (referred to herein equivalently as an "engagement system" or "deployment system") at a distal end a of a delivery member (e.g. micro-catheter) which pushes the coil through the delivery catheter and out of the distal end of the delivery catheter into the delivery site. Example delivery members and engagement/deployment systems are described in U.S. patent application Ser. No. 15/850,993 and U.S. patent application Ser. No. 15/964,857 each incorporated herein by reference.

Some of the challenges that have been associated with properly executing such treatment procedures include ensuring the delivery member and engagement system remain in a stable position throughout a treatment. For example, in some aneurysm treatment applications, as the aneurysm becomes increasingly packed with embolic material, the delivery member can tend to shift due to increasing pushback from the embolic material being implanted. If the delivery member shifts during treatment, a physician may not be able to accurately control placement of embolic material and may choose to cease packing the aneurysm. In such an example, the aneurysm may not be sufficiently packed, which can lead to recanalization. Further, excessive movement or stretching of the delivery member and/or engagement system thereon can result in premature detachment of the embolic coil.

There is therefore a need for improved methods, devices, and systems to provide an implant delivery member and implant engagement system with increased stability.

SUMMARY

It is an object of the present invention to provide systems, devices, and methods to meet the above-stated needs. Generally, it is an object of the present invention to provide a delivery member for delivering and deploying an implantable medical device having a flexible distal portion.

Stiffness of the distal portion of the delivery member can cause the microcatheter used for delivery of the embolic material to pull back out of the aneurysm as the distal end of the delivery member is advanced through the tortuous distal anatomy. If the microcatheter pulls back while advancing the embolic material, the microcatheter may come out of the aneurysm and the physician may lose control of the embolic coil and not be able to accurately control placement of embolic material and may not be able to complete treatment.

Flexibility can be provided by incorporating a length of wound coil along the distal portion of the delivery member. The wound coil can be protected by a flexible polymer sleeve positioned around the outside of the coil. The wound coil can be inhibited from elongating by a stretch resistant tube affixed to hypotubes on either end of the wound coil.

An example delivery member for delivering an implantable medical device to a target location of a body vessel can include a distal hypotube, a support coil section, a proximal hypotube, a flexible sleeve covering the support coil section, and a stretch resistant member extending across the support coil section. The distal hypotube, support coil section, and proximal hypotube can form a contiguous tubular structure having a lumen therethrough. The flexible sleeve can cover some or all of the support coil section to prevent radial expansion of the support coil section and to promote the ability of the support coil section to slide through vasculature. The stretch resistant member can be affixed to the proximal hypotube and the distal hypotube, thereby extending across the entirety of the support coil section.

The delivery member can also include an engagement system that can move to engage and deploy the implantable medical device. The engagement system can include a loop wire and a pull wire. The loop wire can extend through an opening in the implantable medical device and the pull wire can be engaged to the loop wire, thereby engaging the engagement system to the implantable medical device. The pull wire can be positioned within the lumen of the delivery member and can be retracted proximally to disengage the loop wire. Once disengaged from the pull wire, the loop wire can be movable to retract from the opening in the implantable medical device, thereby deploying the implantable medical device.

At least a portion of the distal hypotube can be compressed and can elongate upon movement of the engagement system, when the engagement system is moved to deploy the implantable medical device.

The support coil section can include a non-radiopaque proximal coil, a non-radiopaque distal coil, and a radiopaque central coil positioned between the non-radiopaque coils.

The support coil section can be made from a wire wound to define a portion of the lumen of the delivery member. The wire from which the support coil is made can have a cross-sectional diameter measuring from about 0.8 mil to about 5 mil (about 20 nm to about 130 nm).

The flexible sleeve can include a polymer. The flexible sleeve can include additives to increase lubricity of the polymer.

The flexible sleeve can be affixed to the proximal hypotube and the distal hypotube. The flexible sleeve configured thusly can thereby cover the entirety of the coiled section and at least a portion of the proximal hypotube and/or at least a portion of the distal hypotube.

The stretch resistant member can be an extruded tube.

The support coil section and the distal hypotube can have a length measured from the proximal end of the support coil to the distal end of the distal hypotube that measures between about 30 cm and about 50 cm, or more specifically, about 40 cm.

The proximal hypotube can include a spiral cut portion near its distal end.

An example method for designing or constructing a delivery member such as the example above can include the steps of selecting a first hypotube and a second hypotube, forming a wire coil section between the two hypotubes, extending a stretch resistant member through the lumen of the wire coil section, affixing the stretch resistant member to the first and second hypotubes, selecting a flexible sleeve, covering the support coil section with the flexible sleeve, and attaching the implantable medical device to the distal end of the first hypotube such that the implantable medical device can be detached from the first hypotube during a treatment.

The step of forming the wire coil section can include forming a non-radiopaque proximal coil, forming a non-radiopaque distal coil, and forming a radiopaque central coil extending between the non-radiopaque proximal coil and non-radiopaque distal coil. Alternatively, the wire coil section need not include a radiopaque section. The step of forming the wire coil section can additionally or alternatively include selecting a wire having a diameter measuring about 0.8 mil to about 5 mil (about 20 nm to about 130 mm) and winding the wire to form the wire coil section and to define the lumen of the wire coil section.

The step of selecting the flexible sleeve can include selecting a polymer sleeve having additives to increase lubricity of the polymer.

The step of extending the stretch resistant member through the wire coil lumen can include extending a substantially tubular stretch resistant member through the wire coil lumen.

The step of attaching the implantable medical device to the first hypotube can include compressing the first hypotube and attaching the implantable medical device to the distal end of the compressed first hypotube.

The example method for designing or constructing a delivery member can further include positioning a loop wire within the lumen of the first hypotube and positioning a pull wire to extend through lumens of the first hypotube, wire coil section, and the second hypotube. The step of attaching the implantable medical device can additionally or alternatively include extending the loop wire through an opening in the implantable medical device and engaging the pull wire to a portion of the loop wire extended through the opening of the implantable medical device. The step of attaching the implantable medical device can additionally or alternatively include positioning the pull wire to extend proximally from a proximal end of the second hypotube.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of a cross section of a delivery member according to aspects of the present invention;

FIG. 2A is an illustration of a cross section of a flexible sleeve according to aspects of the present invention;

FIG. 2B is an illustration of a cross section of a stretch resistant tube according to aspects of the present invention;

FIG. 2C is an illustration of a cross section of a wire coil affixed to a distal hypotube and a proximal hypotube according to aspects of the present invention;

FIGS. 3A through 3D are illustrations of an engagement system illustrating a sequence for deploying an implant according to aspects of the present invention;

FIG. 4 is a flow diagram illustrating a method for designing or constructing a delivery member according to aspects of the present invention; and FIG. 5 is a flow diagram illustrating a method for using a delivery system including an example delivery member according to aspects of the present invention.

DETAILED DESCRIPTION

Figure 3C:
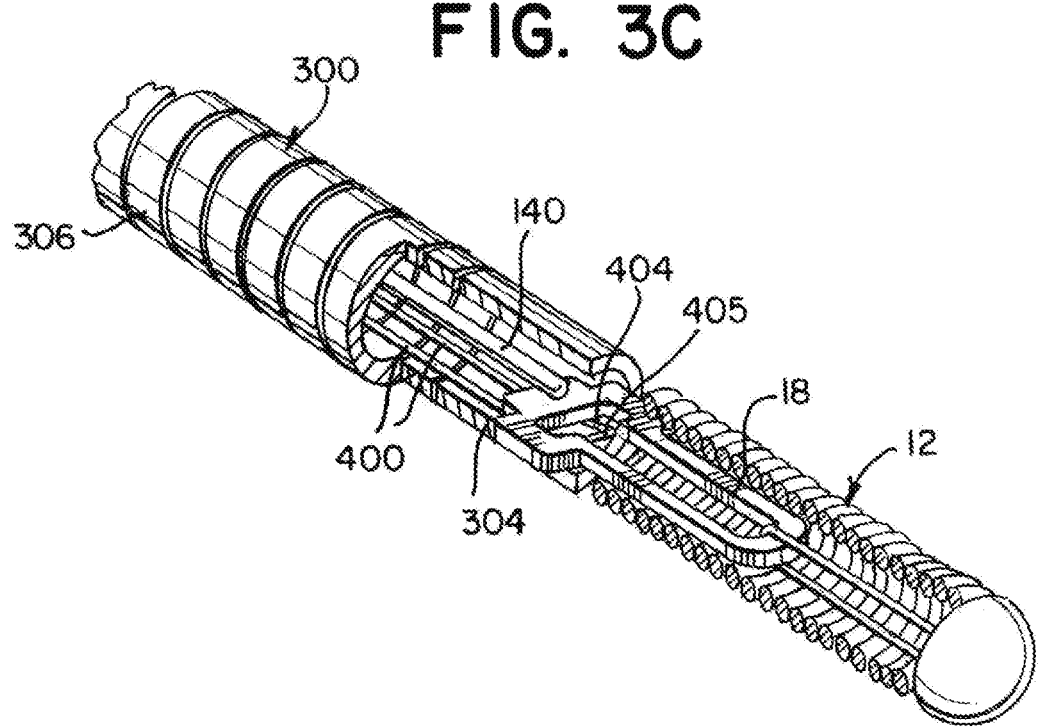

During an intravascular treatment, for instance, an aneurysm occlusion treatment, lack of flexibility of a distal portion of a treatment device delivery member can cause the delivery member to pull back from the treatment site or otherwise move out of position while an implant or other medical treatment device is being placed in an aneurysm or other treatment site. A delivery member and engagement system having a more flexible distal portion can therefore provide a stable system for delivering medical devices in neurovascular anatomy in addition to other applications facing a similar challenge. Flexible structures, however can tend to deform, extend, or expand when navigating tortuous anatomy. Deformation of the delivery member can inhibit the delivery member's ability to navigate to a treatment site and/or effectively deploy the medical device. Elongation of the delivery member can result in premature deployment of the medical device.

An object of the present invention is to provide a delivery member having a highly flexible distal portion that is stretch resistant and structurally stable throughout delivery and deployment of a medical treatment device. For ease of discussion, medical treatment devices are generally referred to herein as an "implant" although, as will be appreciated and understood by a person of ordinary skill in the art, aspects of the present invention can be applied to deliver and deploy medical treatment devices that are not left implanted.

According to the present invention, in some examples, the highly flexible distal portion of the delivery member can include a coiled wire, an outer sleeve, and an inner stretch resistant member. The coiled wire can be formed of a substantially linear wire that is wound in a coil shape and/or a hypotube that is laser cut in a spiral pattern. If the coiled wire is formed from a laser cut hypotube, the spiral can be absent interference cuts connecting windings in the coil so as to provide a more flexible coil. The outer sleeve can inhibit the coiled wire from deforming radially and/or provide a smooth surface against which vascular walls can slide during delivery of an implant. The stretch resistant member can inhibit elongation of the coiled wire during delivery of the implant. The combination of the coiled wire, outer sleeve, and stretch resistant member can therefore provide a distal portion of a delivery member having greater flexibility and greater stability than at least some known delivery members.

Turning to the figures, as illustrated in FIG. 1, an example delivery member 10 can include a proximal tube 100, a coiled section 200, a distal tube 300, a sleeve 500 surrounding the coiled section, and a stretch resistant member 600 within the lumen of the coiled section 200. The proximal tube 100 can extend a majority of the length of the delivery member 10 with the coiled section 200 and distal tube 300 forming a length sufficient to absorb a majority of push-back that can occur during placement of an implant at a treatment site. In some examples, the length can measure between about 30 cm and about 50 cm, or more specifically, about 40 cm. The proximal tube 100 can have a distal end 104 that is connected to a proximal end 202 of the coiled section 200, and the coiled section 200 can have a distal end 204 that is connected to a proximal end 302 of the distal coil 300.

FIG. 2A is a cross sectional view of the sleeve 500. FIG. 2B is a cross sectional view of the stretch resistant member 600. FIG. 2C is a cross sectional view of the assembled proximal tube 100, coiled section 200, and distal tube 300.

The coiled section 200 can be formed separately from the proximal hypotube 100 and/or the distal hypotube 300. The separately formed coiled section 200 can be affixed with welds 712, 714 or other appropriate attachment to the proximal tube 100 and/or the distal tube 300. Alternatively, or additionally, at least a portion of the coiled section can be formed from a spiral laser cut portion of a hypotube. A separately formed coiled section 200 can be made more flexible compared to a spiral cut tube by selecting a wire with a particular cross section (e.g. circular) with a particular diameter D, or by selecting a wire with material properties to increase flexibility. Conversely, a laser cut portion can be more easily fabricated by cutting a single hypotube to form the proximal tube 100, coiled section 200, and distal hypotube 300, reducing or eliminating welds 712, 714 or other attachments. In either case, the wire of the coil 200 can have a diameter D measuring within a range including about 0.8 mils and 5 mils (about 20 nm to about 130 nm).

The coiled section can be formed primarily of a non-radiopaque material such as steel and can include a radiopaque section 216 made of a radiopaque material such as platinum and/or tungsten. The radiopaque section 216 can be positioned between a proximal, non-radiopaque section of the coil 212 and a distal, non-radiopaque section of the coil 214. The radiopaque section 216 can be positioned a predetermined distance from a distal end 304 of the delivery member 10 so that a physician can readily visualize the placement of the distal portion of the delivery member during a treatment procedure. The proximal section 212, radiopaque section 216, and distal section 214 can be concentrically welded.

The coiled section 200 can be surrounded by a flexible sleeve or fused jacket 500, referred generically herein as a "sleeve". The sleeve can inhibit the coil 200 from expanding radially and/or from engaging vascular walls during navigation. The sleeve 500 can include a polymer. The polymer can include additives to increase the lubricity of the sleeve 500 so that the sleeve can easily slide through a body vessel. As illustrated in FIG. 2A, the sleeve 500 can have a wall thickness T measuring within a range including about 0.5 mils and about 2 mils (about 0.01 mm to about 0.05 mm). The sleeve 500 can further be coated with a hydrophilic coating to further minimize friction during intravascular navigation. The sleeve 500 can be fused or glued to the coil 200, the proximal hypotube 100, and/or the distal hypotube 300.

The stretch resistant member 600 can be positioned to inhibit elongation of the coil 200 during intravascular navigation. The stretch resistant member 600 can include a tube sized to fit within the lumen 208 of the coil 200. The stretch resistant tube 600 can also be sized to extend through the entirety of the length of the coil 200, extend with a lumen 108 of the proximal tube 100 and within the lumen 308 of the distal coil 300. The stretch resistant member 600 can be attached to the proximal tube 100 and the distal tube 300 at adhesive joints 702, 704 or other appropriate attachment. The stretch resistant member 600 can remain unattached to the coiled section 200 such that the stretch resistant member 600 and coiled section 200 are able to move independently from each other to some extent.

The delivery member 10 can include a mechanical engagement system for engaging a medical treatment device during delivery to a treatment site that can be actuated mechanically to deploy the treatment device. Mechanically actuated engagement systems often include one or more inner elongated members or pull wires extending through the delivery member that can be manipulated at the proximal end by a physician to deploy a medical treatment device. Such a wire or inner elongated member is referred to herein generically as a "pull wire".

FIGS. 3A through 3D illustrate the delivery member 10 including a mechanical engagement system including a pull wire 140 and a loop wire 400 that can be positioned to secure an implant or other medical treatment device to the delivery member 10 and can be moved to release the medical treatment device from the delivery member 10. The loop wire 400 can be affixed to the distal tube 300 with a weld 408 or other or other suitable attachment (see FIG. 1). The stretch resistant member 600 can be sized to allow a pull wire 140 to pass through the lumens 108, 208, 308 of the proximal tube 100, coiled section 200, and distal tube 300. For instance, the stretch resistant member 600 can be tubular, having a lumen therethrough, and the pull wire 140 can extend through the lumen of the tubular stretch resistant member 600. During manufacture of the stretch resistant member 600, the stretch resistant member 600 can be extruded over the pull wire 140.

The combination of the coil 200, sleeve 500, and stretch resistant member 600 can provide a highly flexible distal portion of a delivery member 10 suitable for navigating tortuous anatomy, including neurovascular blood vessels. The stretch resistant member 600 can support the coil 200 to prevent the coil 200 from significantly extending during navigation of a blood vessel, thereby reducing tension on a pull wire 140 extending therethrough and reducing the likelihood of premature deployment of an attached medical treatment device.

The proximal tube 100 can include a flexible section 106 having material removed to increase flexibility of the flexible section 106. The flexible section 106 can be cut in a spiral pattern. The spiral pattern of the flexible section 106 can lack interference cuts connecting windings within the spiral. The stretch resistant member 600 can extend through the flexible section 106 and be attached to the proximal tube 100 in the proximal direction from the flexible section 106. The stretch resistant member 600 can thereby inhibit elongation of the flexible section 106 of the proximal tube 100 and coiled section 200. The sleeve 500 can cover at least a portion of the flexible section 106 to inhibit deformation of the flexible section and/or reduce friction with vasculature and the flexible section 106 during intravascular navigation. In some examples, the sleeve 500 can cover about 10 cm of the proximal tube 100 approximate and/or including the distal end 104 of the proximal tube 100.

The distal tube 300 can include a compressible portion 306. The compressible portion 306 can be axially adjustable between an elongated condition and a compressed condition. The compressed portion 306 can be formed from a spiral-cut portion of the tube 300, formed by a laser cutting operation. Additionally, or alternatively, the compressible portion can be formed of a wound wire, spiral ribbon, or other arrangement allowing axial adjustment according to the present invention. Preferably, the compressible portion 306 is in the elongated condition at rest and automatically or resiliently returns to the elongated condition from a compressed condition, unless otherwise constrained.

Figure 3D:
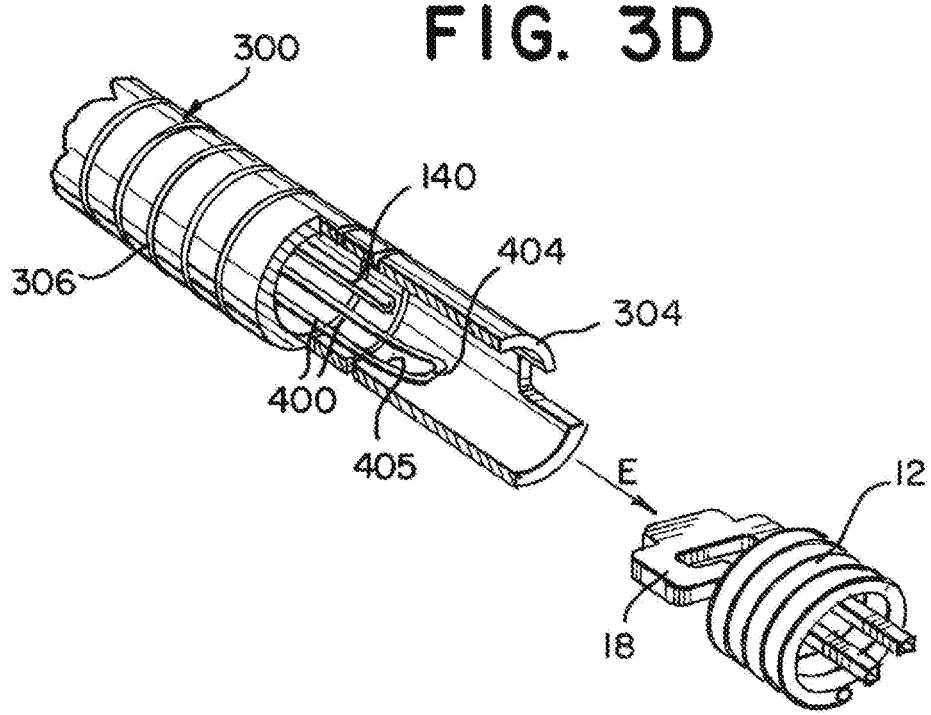

FIGS. 3A-3D, illustrate the detachment of the medical device 12 using a mechanical engagement/deployment system. FIG. 3A illustrates the engagement system 140, 400 locked into the locking portion 18 of the medical device 12. The compressible portion 306 of the distal tube 300 can be compressed and the loop wire 400 opening 405 at a distal end 404 of the loop wire 400 can be placed through the locking portion 18. When the pull wire 140 is put through the opening 405 the medical device 12 is now secure. FIG. 3B illustrates the pull wire 140 being drawn proximally to begin the release sequence for the medical device 12. FIG. 3C illustrates the instant the pull wire 140 exits the opening 405 and is pulled free of the loop wire 400. The distal end 404 of the loop wire 400 falls away and exits the locking portion 18. As can be seen, there is now nothing holding the medical device 12 to the detachment system 10. FIG. 3D illustrates the end of the release sequence. Here, the compressible portion 306 has extended/returned to its original shape and "sprung" forward. An elastic force E is imparted by the distal end 304 of the distal tube 300 to the medical device 12 to "push" it away to ensure a clean separation and delivery of the medical device 12.

Illustrations in the above-described figures depict generally hollow or tubular structures 100, 200, 300, 500, 600 according to the present invention. When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

FIG. 4 is a flow diagram including method steps for constructing or designing a delivery member such as the example delivery members described herein. Referring to the method 800 outlined in FIG. 4, in step 810, a first hypotube, a second hypotube, a flexible sleeve, a wire coil, and a stretch resistant member can be selected. The first hypotube can be a proximal hypotube 100 as described herein or as would otherwise be known to a person of ordinary skill in the art. The second hypotube can be a distal hypotube 300 as described herein or as would otherwise be known to a person of ordinary skill in the art. The flexible sleeve can be a sleeve or fused jacket 500 as described herein or as otherwise known to a person of ordinary skill in the art. The wire coil can include the support coil, coiled section 200 as described herein or as otherwise known to a person of ordinary skill in the art. The stretch resistant member can be a stretch resistant member 600 as described herein or as otherwise known to a person of ordinary skill in the art.

In step 820, the stretch resistant member can be positioned in the lumen of the wire coil. In step 820, the stretch resistant member that is positioned can be substantially tubular. In step 830, the first hypotube, wire coil, and second hypotube can be attached to each other. In step 840, the stretch resistant member is attached to the first hypotube and the second hypotube. The first hypotube, wire coil, and second hypotube can be attached as illustrated and described herein or by other means as would be understood by a person of ordinary skill in the art. Steps 820, 830, and 840 need not be performed in that order and can be performed simultaneously. For instance, the stretch resistant member can be attached to one of the first and second hypotubes as indicated in step 840, then the hypotube to which the stretch resistant member is attached can be attached to the wire coil as indicated in step 830, then the stretch resistant member can be positioned through the wire coil as indicated in step 820, then the other of the hypotubes can be attached to the wire coil as indicated in step 830, then the stretch resistant member can be attached to that other hypotube as indicated in step 840.

In step 850, the wire coil can be covered with the flexible sleeve. The flexible sleeve can cover some or all of the outer surface of the wire coil. Step 850 can also include the step of fusing the flexible sleeve to the wire coil and/or otherwise affixing the flexible sleeve to the delivery member. If the second hypotube has a flexible section, in step 850, the flexible sleeve can also be positioned to cover at least a portion of the flexible section.

In step 860, an implant can be detachably attached to the distal end of the first hypotube. In step 860, the implant can be attached by positioning a loop wire within the first hypotube, positioning a pull wire to extend through the first hypotube, coiled wire, and second hypotube, and securing the implant with the loop wire and the pull wire. The pull wire can be extended from the proximal end of the second hypotube. If the first hypotube has a compressible portion, in step 860, the compressible portion can be compressed, and the implant can be attached to delivery member while the compressible portion is compressed.

FIG. 5 is a flow diagram including method steps for administering an intravascular treatment using a system including a delivery member such as the example delivery members described herein. Referring to the method 900 outlined in FIG. 5, in step 910 a system having a distal hypotube, proximal hypotube, coiled section co-axially positioned in between the hypotubes, a flexible sleeve covering the coiled section, a stretch resistant member positioned within the coiled section, and a medical treatment device attached to or near the distal hypotube can be selected. The system can be suitable for intravascular treatments such as described and illustrated herein or as otherwise known to a person of ordinary skill in the art.

In step 920, the system can be moved through a catheter to a treatment site such as the site of an aneurysm or other abnormality in a blood vessel. In step 930, the system can be flexed as it is moved through the catheter. In step 940, the coiled section of the system can be prevented from deforming by the flexible sleeve and the stretch resistant member; the flexible sleeve can inhibit the coiled section from deforming radially while the stretch resistant member can inhibit the coil from extending longitudinally.

In step 950, the medical treatment device can be deployed. In the case that the medical treatment device is an implant, in step 950 the implant can be detached. In step 960, the distal tube can extend to push the medical treatment device away from the distal tube. In the case that the medical treatment device is an implant detached in step 950, in step 960, the detached implant can be ejected away from the distal tube in response to the expansion of the distal tube.

The descriptions contained herein are examples of embodiments of the invention and are not intended in any way to limit the scope of the invention. As described herein, the invention contemplates many variations and modifications of the delivery system, delivery member, and engagement system, including alternative configurations of components, alternative materials, alternative medical treatment devices, alternative means for deploying the medical treatment device, alternative geometries of individual components, alternative means for attaching component parts, etc. These modifications would be apparent to those having ordinary skill in the art to which this invention relates and are intended to be within the scope of the claims which follow.

What is claimed is:

1. A delivery member for delivering an implantable medical device to a target location of a body vessel, the delivery member comprising: a distal hypotube comprising a distal end shaped to receive the implantable medical device; a support coil section terminating at a proximal most end and a distal most end, the distal most end directly affixed to a proximal most end of the distal hypotube; a proximal hypotube comprising a distal most end directly affixed to the proximal most end of the support coil section; a lumen extending through the distal hypotube, the support coil section, and the proximal hypotube; a flexible sleeve covering at least a majority of an outer surface of the support coil section; and a stretch resistant member extending through a portion of the lumen, the stretch resistant member affixed to the proximal hypotube and affixed to the distal hypotube.

2. The delivery member of claim 1, wherein the support coil section comprises: a non-radiopaque proximal coil extending from the proximal most end of the support coil section; a non-radiopaque distal coil extending from the distal most end of the support coil section; and a radiopaque central coil extending between the non-radiopaque proximal coil and the non-radiopaque distal coil.

3. The delivery member of claim 1, where in the support coil section comprises:
a wire wound to form the support coil section and defining a portion of the lumen, the wire comprising a diameter measuring from about 0.0008 inch to about 0.005 inch.

4. The delivery member of claim 1,
wherein the flexible sleeve comprises a polymer, and
wherein the flexible sleeve comprises additives effective to increase a lubricity of the polymer.

5. The delivery member of claim 1, wherein the flexible sleeve is affixed to the proximal hypotube and the distal hypotube.

6. The delivery member of claim 1, wherein the stretch resistant member is an extruded tube.

7. The delivery member of claim 1, wherein the delivery member comprises a length measurable from the proximal most end of the support coil section to the distal most end of the distal hypotube, and wherein the length measures about 40 cm.

8. The delivery member of claim 1, wherein the proximal hypotube comprises a spiral cut portion approximate a distal most end of the proximal hypotube.

9. The delivery member of claim 1, wherein the support coil section extends entirely between the proximal most end of the distal hypotube and the distal most end of the proximal hypotube.

10. The delivery member of claim 1, wherein the support coil is configured to provide structural support to the distal hypotube such that the support coil and distal hypotube are configured to absorb a majority of push-back due to release of the implantable medical device.

11. The delivery member of claim 1, further comprising: an engagement system movable to engage and deploy the implantable medical device engaged at the distal most end of the distal hypotube, the engagement system comprising: a loop wire extended through an opening in the implantable medical device thereby engaging the engagement system to the implantable medical device and movable to retract from the opening in the implantable, medical device to deploy the implantable medical device, and a pull wire extended through the lumen, engaged to the loop wire thereby engaging the engagement system to the implantable medical device, and movable to retract proximally to disengage the loop wire to deploy the implantable medical device.

12. The delivery member of claim 11,
wherein the distal hypotube comprises a compressible portion movable from a compressed condition to an elongated condition, and
wherein the engagement system maintains the compressible portion in the compressed condition when engaged to the implantable medical device.

13. A method of constructing a delivery member for delivering an implantable medical device, the method comprising: selecting a first hypotube comprising a first lumen therethrough; selecting a second hypotube comprising a second lumen therethrough; forming a wire coil section extending entirely between a distal most end of the second hypotube and a proximal most end of the first hypotube such that a distal most end of the wire coil section is directly affixed to the proximal most end of the first hypotube and the proximal most end of the wire coil section directly affixed to the distal most end of the second hypotube and the wire coil section defines a third lumen therethrough; extending a stretch resistant member through the third lumen; affixing the stretch resistant member to the first hypotube and second hypotube; selecting a flexible sleeve; covering at least a majority of the outer surface of the support coil section with the flexible sleeve; and detachably attaching the implantable medical device to the delivery member approximate a distal end of the first hypotube.

14. The method of claim 13, wherein the forming of the wire coil section further comprises: forming a non-radiopaque proximal coil extending distally from the distal most end of the second hypotube; forming a non-radiopaque distal coil extending proximally from the proximal most end of the first hypotube; and forming a radiopaque central coil extending between the non-radiopaque proximal coil and the non-radiopaque distal coil.

15. The method of claim 13, wherein the forming of the wire coil section further comprises: selecting a wire comprising a diameter measuring from about 0.0008 inch to about 0.005 inch; and winding the wire to form the wire coil section and define the lumen therethrough.

16. The method of claim 13, wherein the selecting of the flexible sleeve further comprises: selecting the flexible sleeve comprising a polymer and additives effective to increase the lubricity of the polymer.

17. The method of claim 13, wherein the extending of the stretch resistant member through the third lumen further comprises: extending the stretch resistant member that is substantially tubular through the third lumen.

18. The method of claim 13, wherein the detachably attaching the implantable medical device to the delivery member approximate a distal end of the first hypotube further comprises: compressing the first hypotube; and detachably attaching the implantable medical device to the delivery member approximate the distal end of the compressed first hypotube.

19. The method of claim 13, further comprising:
   positioning a loop wire within the first lumen; and
   positioning a pull wire to extend through the first lumen, third lumen, and first lumen,
      wherein the step of detachably attaching the implantable medical device to a distal end of the first hypotube further comprises:
         extending the loop wire through an opening in the implantable medical device; and
         engaging the pull wire to a portion of the loop wire extended through the opening in the implantable medical device.

20. The method of claim 19, wherein the detachably attaching the implantable medical device to a distal end of the first hypotube further comprises: positioning the pull wire to extend proximally from a proximal end of the second hypotube.

* * * * *